United States Patent
Mehra et al.

(10) Patent No.: US 9,599,609 B2
(45) Date of Patent: *Mar. 21, 2017

(54) LATERAL FLOW STRIP ASSAY WITH IMMOBILIZED CONJUGATE

(71) Applicant: Abaxis, Inc., Union City, CA (US)

(72) Inventors: Rajesh K. Mehra, Hayward, CA (US); Kenneth P. Aron, San Francisco, CA (US)

(73) Assignee: ABAXIS, INC., Union City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/469,347

(22) Filed: Aug. 26, 2014

(65) Prior Publication Data

US 2015/0104810 A1    Apr. 16, 2015

Related U.S. Application Data

(63) Continuation of application No. 12/630,777, filed on Dec. 3, 2009, now Pat. No. 8,846,319.

(60) Provisional application No. 61/119,612, filed on Dec. 3, 2008.

(51) Int. Cl.
| | |
|---|---|
| *C12M 1/34* | (2006.01) |
| *C12M 1/00* | (2006.01) |
| *C12Q 1/68* | (2006.01) |
| *G01N 33/53* | (2006.01) |
| *G01N 31/22* | (2006.01) |
| *G01N 21/77* | (2006.01) |
| *G01N 33/566* | (2006.01) |
| *G01N 33/543* | (2006.01) |

(52) U.S. Cl.
CPC . *G01N 33/54313* (2013.01); *G01N 33/54393* (2013.01)

(58) Field of Classification Search
CPC ............. C12Q 1/68; G01N 33/53; B82Y 5/00
USPC ............ 435/6.1, 7.1, 283.1, 287.1; 422/430; 436/169, 501; 977/773
See application file for complete search history.

(56) References Cited

U.S. PATENT DOCUMENTS

| | | | |
|---|---|---|---|
| 4,313,734 | A | 2/1982 | Leuvering |
| 5,102,788 | A | 4/1992 | Cole |
| 6,699,724 | B1 | 3/2004 | West |
| 7,344,893 | B2 | 3/2008 | Kirkegaard |
| 7,932,099 | B2 | 4/2011 | Egan et al. |
| 8,846,319 | B2 | 9/2014 | Mehra et al. |
| 2002/0004246 | A1 | 1/2002 | Daniels et al. |
| 2004/0110167 | A1 | 6/2004 | Gerdes et al. |
| 2005/0208593 | A1 | 9/2005 | Vail et al. |
| 2005/0214951 | A1 | 9/2005 | Nahm et al. |
| 2006/0078986 | A1 | 4/2006 | Ly et al. |
| 2006/0154315 | A1 | 7/2006 | Cheng et al. |
| 2006/0166374 | A1 | 7/2006 | Hubscher et al. |
| 2006/0246601 | A1 | 11/2006 | Song et al. |
| 2006/0286684 | A1 | 12/2006 | Brennan et al. |
| 2007/0059203 | A1 | 3/2007 | Burrell et al. |
| 2007/0134815 | A1 | 6/2007 | Chamberlin et al. |
| 2008/0032420 | A1 | 2/2008 | Lambert et al. |
| 2010/0136566 | A1 | 6/2010 | Mehra |

FOREIGN PATENT DOCUMENTS

WO    WO 2006/039542    4/2006

OTHER PUBLICATIONS

Huang, Gold nanoparticle-based immunochromatographic assay for the detection of *Staphylococcus aureus*, 2007, Sensors and Actuators B, 127, 335-340.*

Campbell et al, Development and validation of a lateral flow device for the detection of nicarbazin contamination in poultry feeds, 2007, J. Agric. Food Chem., 55, 2497-2593.

Qdot brochure, down loaded on Apr. 29, 2011 from the Invitrogen Website, pp. 1- 16.

Pubmed search results, down loaded from the internet [www.ncbi.nlm.nih.gov/pubmed], p. 1 , printed on Oct. 29, 2011.

Corstjens et al, Lateral-flow and up-converting phosphor reporters to detect single-stranded nucleic acids in a sandwich-hybridization assay, 2003, 312, 191-200.

P. Englebienne, A. Van Hoonacker, and J. Valsamis, "Rapid Homogeneous Immunoassay for Human Ferritin in the Cobas Mira Using Colloidal Gold as the Reporter Reagent," Clin. Chem. 46:12, 2000 (2000).

J. Chandler, N. Robinson and K. Whiting, "Handling false signals in gold-based rapid tests." IVD Tech. (2001).

V. K. Gasparyan, "Hen egg immunoglobulin Y in colloidal gold agglutination assay: comparison with rabbit immunoglobulin G," J. Clin. Lab. Anal. 19:3, 124 (2005).

Z. Jiang, S. Sun, A. Liang, W. Huang and A. Qin, "Gold-Labeled Nanoparticle-Based Immunoresonance Scattering Spectral Assay for Trace Apolipoprotein AI and Apolipoprotein B," Clin. Chem. 52:7, 1389 (2006).

C. Guarise, L. Pasquato, V. D. Filippis and P. Scrimin, "Gold Nanoparticles-based Protease Assay," Proc. Natl. Acad. Sci. 103:11, 3978-3982 (2006).

S. Goto, S. Nagahiro, Y. Ushio, and W. Hofer, "A Simple Enhancement Method for the Silver-Gold-intensified Diaminobenzidine Reaction in the Light Microscopic Immunoperoxidase Technique," The Journal of Histochemistry and Cytochemistry, 40:9, 1423-1425 (1992).

Chang, International Search Report and Written Opinion for PCT/US2009/066648, mailed Aug. 18, 2010.

* cited by examiner

*Primary Examiner* — Narayan Bhat
(74) *Attorney, Agent, or Firm* — Cooley LLP

(57) ABSTRACT

The present invention discloses analyte detection devices for detecting one or more analytes present in test samples, especially biological samples. In particular, the devices of the invention are lateral flow assay devices comprising immobilized metal nanoparticle conjugates as the detection means. Methods of using the devices and kits comprising the devices are also described.

20 Claims, 3 Drawing Sheets

LATERAL FLOW STRIP ASSAY WITH IMMOBILIZED CONJUGATE

This application is a Continuation of U.S. patent application Ser. No. 12/630,777 filed Dec. 3, 2009, which claims priority to U.S. Provisional Application No. 61/119,612, filed Dec. 3, 2008, all of which are incorporated herein by reference in their entireties.

FIELD OF THE INVENTION

The present invention relates to lateral flow assay devices for detecting a target analyte in a sample. In particular, the present invention is directed to lateral flow assay devices in which the presence of the analyte is detected by immobilized analyte binding partners coupled to detectable entities, e.g., metallic nanoparticles or metallic nanoshells.

BACKGROUND OF THE INVENTION

Methods and devices to detect target analytes in samples, particularly biological samples, have taken advantage of the specific interactions between biological molecules, such as the interactions between antigen-antibody (or part of antibody, e.g., Fv), ligand-receptor, enzyme-substrate, binding protein-nucleic acid or aptamer, and hybridization of nucleic acid molecules. These interactions allow for the analyte to be isolated or captured from other components in the sample.

A common type of device that incorporates the use of such biological interactions is a lateral flow assay device or strip assay device. Such assay devices typically comprise a reagent pad that contains a binding partner for the analyte of interest coupled to a detectable label (i.e. labeled conjugates) and a porous membrane on which a capture protein (e.g. antibody or antigen) capable of binding the analyte of interest is immobilized. Labeled conjugates that are commonly used in these types of assay devices are antibodies or antigens coupled to gold nanoparticles or colored latex particles. A liquid sample applied to the device travels by capillary action through the reagent pad where any analyte present in the sample binds to the labeled conjugate forming a complex. The complex continues to migrate through the porous membrane to the region where the capture protein is immobilized at which point the complex of analyte and labeled conjugate will bind to the capture protein. The unreacted sample passes through the immobilized capture protein region without binding. The presence of the analyte is then determined by detecting the labeled conjugate in the capture region of the device (e.g. by a color change). Although these devices are amenable for use as rapid clinical tests for some analytes, the nature of these assay devices prevents single-step amplification of the detection signal, thus making such devices inadequate for the detection of a number of analytes that require greater sensitivity.

One method that has been previously employed to enhance the sensitivity of assays that utilize specific biological interactions for the detection of analytes in samples is the use of enzyme labels. The enzyme-linked immunosorbent assay (ELISA) format exemplifies such a method. In these assays, an antibody or antigen capable of binding an analyte of interest is immobilized on the bottom of a microplate well. Sample is added to the well followed by one or more wash steps. A second antibody or antigen coupled to an enzyme is subsequently added to the well. After additional wash steps, a substrate that can be converted by the enzyme into a chromogenic or fluorescent substance is added to the well, and the presence of analyte is determined by detecting the chromogenic or fluorescent substance. Enzyme-labeled conjugates have been incorporated in lateral flow assays to improve their sensitivity. However, such assays require additional steps to add enzyme substrate or wash away unreacted conjugates. Consequently these assays require longer time than lateral flow assays.

Thus, there is a need in the art for additional lateral flow assay devices, e.g., devices that offer greater detection sensitivity. The development of one-step, e.g., rapid lateral flow assay devices with built-in amplification is desirable.

SUMMARY OF THE INVENTION

The binding of substances to a metallic surface or to binding partners on a metallic surface, e.g., binding partners attached to, adsorbed onto or chemically linked to a metallic surface can be detected by changes in the local refractive index, which is observed by shifts in the absorbance spectra. These spectral shifts caused by the phenomenon of surface plasmon resonance are exquisitely sensitive to the interactions of the surface plasmons with the boundary of the metallic surface and the surrounding medium. As such, sensitive assays, including lateral flow assays, for detecting a target analyte in a sample have been developed based on techniques utilizing surface plasmon resonance and the related phenomenon of localized surface plasmon resonance, which occurs with metallic nanoparticles.

The present invention is based in part on the discovery that metallic particle conjugates of a binding entity immobilized on a surface are capable of undergoing unique spectral changes upon interaction of the binding entity with its binding partner. Accordingly, the present invention provides an analyte detection device in which a binding partner coupled to a metallic particle, e.g., metallic nanoparticle or metallic nanoshell is immobilized to a surface and acts to capture target analyte present in the sample. Without any technical limitation, applicants believe that using metallic particle conjugate, e.g., metallic nanoparticle conjugate as the capture entity allows for the opportunity to amplify the detection signal produced by the interaction of target analyte with conjugate, e.g., by incorporating accelerants, such as polymers, into such interaction which can enhance the spectral shift of the nanoparticle conjugates upon binding of the conjugate to the target analyte.

In one embodiment, the present invention provides an analyte detection device comprising a detecting complex immobilized on a first surface, wherein the detecting complex comprises a first binding partner coupled to a detectable entity, wherein the first binding partner is capable of forming a complex with a target analyte, and wherein the detecting complex is formed prior to being immobilized on the first surface. The first surface can be a porous surface. In some embodiments, the detectable entity is a metallic nanoparticle or metallic nanoshell.

In further embodiments of the invention, the device further comprises a sample pad in fluid communication with the first surface. The sample pad can contain one or more dried components, such as buffers, detergents, blocking agents, neutralizing agents, and accelerants. In another embodiment, the device can further comprise a sample pad and an adsorbent pad, both of which are in operable fluid communication with the first surface.

In some embodiments, the device further comprises a sample pad and a reagent pad, both of which are in operable fluid communication with the first surface. In other embodiments, the device further comprises a sample pad, a reagent pad, and an adsorbent pad, all of which are in operable fluid communication with the first surface. The reagent pad can comprise a second binding partner capable of forming a complex with the target analyte. The first binding partner and the second binding partner can be an antibody or a region thereof (e.g., Fv, single chain, CDR, antibody expressed in phage display, etc.), receptor, ligand, polynucleotide, oligonucleotide, aptamer, polypeptide, glycopeptide, lipoprotein, or nucleoprotein. In one embodiment, the reagent pad is positioned between the sample pad and the first surface.

The devices of the invention can further comprise a control zone in operable fluid communication with the sample pad, reagent pad and the first surface. The control zone is capable of indicating a positive control for the device. In one embodiment, the control zone contains a control detecting complex capable of binding a component naturally found in the sample, but unique from the target analyte. In another embodiment, the control detecting complex binds to a component that has been artificially added to the sample.

In some embodiments of the invention, the device is positioned in an enclosed housing. The housing can comprise a sample port positioned over the sample pad and/or a test window positioned over the first surface. In one embodiment, the housing comprises one or more vents to facilitate fluid movement through the device.

The present invention also encompasses devices for the simultaneous detection of multiple analytes. In one embodiment, the device comprises a first detecting complex and a second detecting complex immobilized on at least one surface, wherein the first detecting complex comprises a first binding partner coupled to a first detectable entity, wherein the second detecting complex comprises a second binding partner coupled to a second detectable entity, wherein the first binding partner is capable of forming a complex with a first target analyte and the second binding partner is capable of forming a complex with a second target analyte, and wherein the first detecting complex and the second detecting complex are formed prior to being immobilized on the at least one surface. The first detectable complex and the second detectable complex can be immobilized on the same surface. In another embodiment, the device further comprises a second surface, wherein the second surface is adjacent to the first surface, and wherein the first detectable complex is immobilized on the first surface and the second detectable complex is immobilized on the second surface.

The present invention also contemplates a method of detecting a target analyte in a test sample using the devices of the invention. In one embodiment, the method comprises contacting the test sample with the first surface of the device and detecting a signal corresponding to the binding of the target analyte to the detecting complex, wherein the presence of the signal is indicative of the presence of the target analyte. In another embodiment, the method comprises contacting the sample with the sample pad of the inventive device and detecting a signal corresponding to the binding of the target analyte to the detecting complex, wherein the presence of the signal is indicative of the presence of the target analyte. In some embodiments, the method further comprises contacting the sample pad with an enhancing agent. The signal that is detected can be a spectral shift, and the signal can be detected by measuring a change in absorbance of the signal.

The present invention also includes a kit comprising an analyte detection device of the invention and instructions for using the device to detect an analyte in a test sample. The kit can further comprise means for collecting samples, buffers for extracting samples from solid substances, and enhancing agents.

BRIEF DESCRIPTION OF THE DRAWINGS

FIG. 2A shows a configuration in which the device comprises multiple surfaces on which a different detecting complex (I, II, and III) is immobilized. Each of the different detecting complexes is capable of binding a unique target analyte. FIG. 2B depicts a second configuration in which different detecting complexes (I, II, and III) are immobilized on the same surface. The devices can comprise sample pads, reagent pads, and sample ports as shown. In addition, the devices can also incorporate adsorbent pads and/or one or more control zones as described herein.

DETAILED DESCRIPTION OF THE INVENTION

Figure 1:
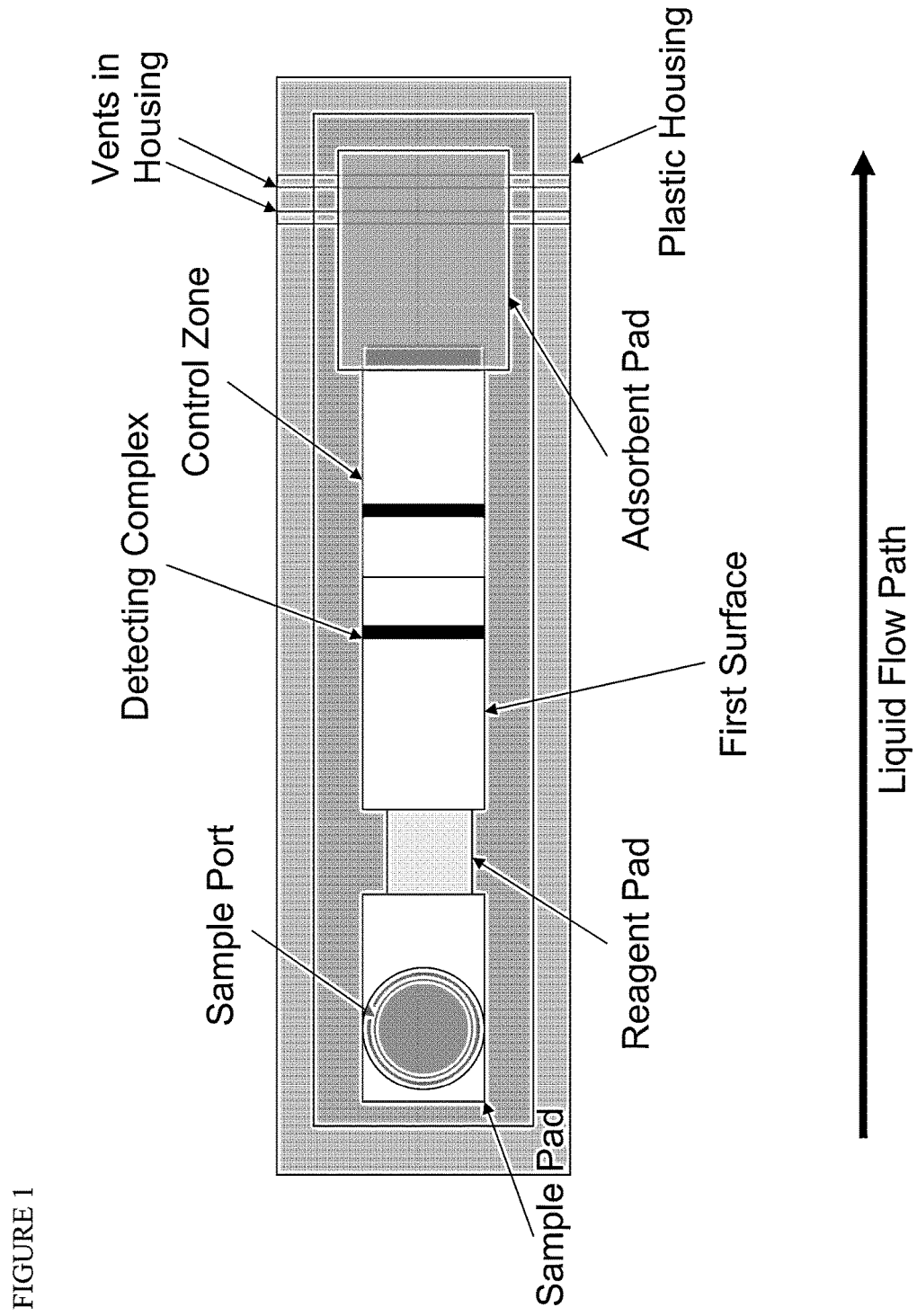
FIG. 1 depicts a top view of one embodiment of the analyte detection device of the invention. The device is enclosed in a plastic housing as shown by the rectangular frame surrounding the components of the device. The housing can contain a sample port positioned above the sample pad at the first end of the plastic housing to facilitate application of the sample to the device. The housing can contain one or more vents as illustrated by the parallel black lines at the second end of the plastic housing in the figure. The sample pad, reagent pad, first surface and adsorbent pad are all in fluid communication such that the flow path of liquid applied to the sample pad extends through all components to end in the adsorbent pad.

The present invention is based, in part on the discovery that metallic particle conjugates of a binding entity immobilized on a surface are capable of undergoing unique spectral changes upon interaction of the binding entity with its binding partner. Accordingly, the present invention provides an analyte detection device in which a binding partner coupled to a metallic particle, e.g., metallic nanoparticle or metallic nanoshell is immobilized to a surface and acts to capture target analyte present in a sample.

In one aspect, the present invention provides an analyte detection device comprising a detecting complex immobilized to a surface, wherein the detecting complex comprises a binding partner for a target analyte coupled to a detectable entity (e.g. metallic nanoparticle or metallic nanoshell). In one embodiment, the device comprises a detecting complex immobilized on a first surface, wherein the detecting complex comprises a first binding partner coupled to a detectable entity, wherein the first binding partner is capable of forming a complex with a target analyte, and wherein the detecting complex is formed prior to being immobilized on the first surface.

The first surface is preferably a porous material. A "porous" material refers to a material containing a plurality of interstices or pores through which liquid easily flows. The porous material can be made from natural or synthetic substances. Suitable porous materials for use in the device of the present invention include, but are not limited to, nitrocellulosic material, polyvinylidene fluoride (PVDF), polyethylene material (e.g. Porex®), nylon, cellulose acetate, polyester material, polyethersulfone (PES) material, or polysulfone material. Other appropriate porous materials that can be used in the inventive devices are known to those skilled in the art. In some embodiments, a non-porous material can be used as a backing for the first surface.

The detecting complex, which is immobilized onto the first surface, comprises a first binding partner coupled to a detectable entity. The first binding partner can be any entity that is capable of specifically binding a target analyte. In some embodiments, the first binding partner is a biological macromolecule, including but not limited to an antibody or a region thereof, a receptor, a ligand, a polynucleotide, an aptamer, a polypeptide, a glycopeptide, a lipoprotein, or a nucleoprotein. In one embodiment, the first binding partner is an antibody.

As used herein, "detectable entity" is an entity that exhibits wavelength selective absorption in the ultra-violet, visible, or near infrared electromagnetic spectrum and scatters incident radiation. In one embodiment, the detectable entity is a metallic nanoparticle or metallic nanoshell. Various types of metallic nanoparticles that can be coupled to the first binding partner include, but are not limited to, gold particles, silver particles, copper particles, platinum particles, cadmium particles, composite particles (e.g. silver and gold or copper and silver), and gold hollow spheres. In some embodiments, the detectable entity is a gold nanoparticle. Additionally, metal nanoshells as described in U.S. Pat. No. 6,699,724, which is herein incorporated by reference in its entirety, can also be used as the labeling particles. Metal nanoshells are particles comprised of a dielectric core and a metallic coating that have a defined core radius to shell thickness ratio. The core can be comprised of a variety of materials including silicon dioxide, gold sulfide, titanium dioxide, and polystyrene. Suitable metals for the shell include gold, silver, copper, platinum, palladium, lead, and iron. Gold-coated silica nanoshells or silica-coated gold shells are preferred in some embodiments.

Methods of coupling metallic nanoparticles or metallic nanoshells to a binding partner are well known in the art. One such method is by passive adsorption. This method involves adjusting the pH of the metal colloid solution to a pH at which the protein or other binding partner to be labeled has a positive charge, mixing the metal colloid solution with the binding partner solution, and centrifuging the resultant mixture. The labeled binding partner (e.g. protein) is then obtained by removing the supernatant and resolubilizing the precipitate. Other methods of conjugating macromolecules to metal nanoparticles or nanoshells are known to the skilled artisan, who can select the proper method based on the type of desired nanoparticle to be used and the type of macromolecule to be labeled. In some embodiments, the binding partner can be coupled to the metallic nanoparticle or metallic nanoshell indirectly through a larger carrier molecule or protein. Such indirect coupling is particularly useful when the binding reagent is small, such as hormones, drugs, and other small molecules less than 10 kD. Preferably, the carrier protein is not capable of specific interaction with the target analyte. In some embodiments, the first binding partner is coupled to the detectable entity to form a detecting complex prior to the immobilization of the complex on the first surface.

The detecting complex can be immobilized on the first surface by a variety of procedures. The detecting complex can be striped, deposited, or printed on the first surface followed by drying of the first surface to facilitate immobilization. In one embodiment, the detecting complex is immobilized on the first surface by depositing the detecting complex on the first surface. Immobilization of the detecting complex can take place through adsorption or covalent bonding. Depending on the nature of the first surface (e.g. type of porous material), methods of derivatization to facilitate the formation of covalent bonds between the first surface and the detecting complex can be used. Methods of derivatization can include treating the first surface with a compound, such as glutaraldehyde or carbodiimide and applying the detecting complex. Other physical, chemical, or biological methods of immobilizing a macromolecular conjugate either directly or indirectly to a porous material are known in the art and can be used to immobilize the detecting complex to the first surface in the device of the invention.

In some embodiments of the invention, the device further comprises a sample pad in fluid communication with the first surface. As used herein, "fluid communication" or "operable fluid communication" refers to the ability of a liquid to flow or travel between two materials or surfaces. Fluid communication can be established between two porous materials or between a porous material and a non-porous material. In the latter situation, the non-porous material can form a channel or conduit by which fluid can flow by capillary action to establish fluid communication between the non-porous material and the porous material. The sample pad can be manufactured from one of several materials, including but not limited to, polyester, polyacrylic, other polymeric materials, or glass fiber.

In another embodiment of the invention, the device further comprises a sample pad and an adsorbent pad, both of which are in operable fluid communication with the first surface. Preferably, the first surface is positioned between the sample pad and the adsorbent pad. The adsorbent can be constructed from cellulose materials or the like. The adsorbent pad can function to facilitate the movement of fluids through the device and to remove excess fluid from other components of the device, such as the sample pad and the first surface.

In still another embodiment, the device further comprises a sample pad and a reagent pad, both of which are in operable fluid communication with the first surface. The reagent pad can contain a second binding partner capable of forming a complex with the target analyte. The second binding partner can be a biological macromolecule, such as an antibody, a receptor, a ligand, a polynucleotide, a polypeptide, a glycopeptide, a lipoprotein, or a nucleoprotein. The second binding partner can be the same type of reagent as the first binding partner, but preferably interacts with the target analyte at a location distinct from that as the first binding partner. By way of example, the first binding partner and the second binding partner can both be antibodies that recognize a target analyte, but the epitope to which the first binding partner binds the target analyte is separate from the epitope to which the second binding partner binds the target analyte.

In some embodiments, the reagent pad is positioned between the sample pad and the first surface. Such a configuration allows for any analyte present in the sample to interact with the second binding partner before contacting the detecting complex immobilized on the first surface. The second binding partner can be dried and subsequently deposited on the reagent pad. The reagent pad can be constructed of similar materials as the sample pad and can contain one or more excipients to stabilize the dried binding partner. Such excipients will depend on the type of binding partner deposited on the reagent pad, but can include albumins, caseins, gelatin, or polymeric stabilizers such as polyvinylpyrrolidone or polyvinyl alcohol.

In other embodiments, the device further comprises a sample pad, a reagent pad, and an adsorbent pad, all of which are in operable fluid communication with the first surface. One such embodiment is illustrated in FIG. 1. A liquid sample placed on the sample pad passes through the reagent pad contacting secondary binding partner that can be dried on the reagent pad. The sample continues to flow to the first surface, wherein analyte or analyte complexed with the secondary binding partner interacts with the detecting complex immobilized on the first surface. The sample containing unreacted components flows into the adsorbent pad at the end of the liquid flow path.

In another embodiment of the invention, the first surface of the analytical detection device can comprise an accelerant. An "accelerant" is an agent that facilitates the spectral shift of a detecting complex produced by the specific binding of an analyte to the detecting complex. Suitable accelerants include, but are not limited to, polyethylene glycol, polyvinylpyrrolidone, polyvinyl alcohol, other like polymers, and mixtures thereof. Preferably, the portion of the first surface containing the accelerant does not overlap with the region comprising the immobilized detecting complex. In one embodiment, the accelerant is deposited on a portion of the first surface that is contiguous and upstream to the portion of the first surface comprising the immobilized detecting complex such that liquid sample moving through the first surface will mobilize the accelerant and carry the accelerant to the immobilized detecting complex.

In further embodiments of the invention, the first surface can comprise a blocking agent, a neutralizing agent, or combination thereof. A "blocking agent" is an agent that prevents the association of proteins present in the sample with the detecting complex, the second binding partner, if present, and/or target analyte. Blocking agents are typically proteins themselves and can include, but are not limited to, bovine serum albumin, casein, gelatin, ovalbumin, gamma-globulins, and IgG from non-immunized animals. A "neutralizing agent" is an agent that reduces the chemical reactivity of at least one interfering species. An interfering species can be a biological molecule or other compound present in a sample that exhibits a non-specific binding affinity to the detecting complex. Non-limiting examples of neutralizing agents include alkylating agents, such as iodoacetamide, iodoacetate, N-ethylmaleimide, PEG-maleimide, ethylmethanesulfonate, 4-vinylpyridine, nitrogen mustards, nitrosourea compounds, dacarbazine, and temozolomide. Neutralizing agents are described in detail in co-pending U.S. Provisional Application No. 61/079,777, filed Jul. 10, 2008, which is herein incorporated by reference in its entirety. The blocking agents and/or neutralizing agents can be co-located with the immobilized detecting complex on the first surface. The agents can be lyophilized and subsequently deposited on the first surface. Alternatively, the first surface can be treated with the blocking agents and/or neutralizing agents following immobilization of the detecting complex.

In additional embodiments, the sample pad can comprise an accelerant, blocking agent, neutralizing agent, or a combination thereof. In some embodiments, the sample pad comprises one or more dried buffers or detergents or a combination thereof. Non-limiting examples of suitable detergents that can be included in the sample pad are Tween-20, Triton X-100, saponin, zwittergents based on sulfotaines, CHAPS, octyl glucosides, and lauryl sulfates. Standard buffers typically used in lateral flow assays, such as Tris, Hepes, imidazole, or phosphate, can be dried into the sample pads of the devices of the instant invention.

In still other embodiments of the invention, the device further comprises a control zone in operable fluid communication with the sample pad, reagent pad, and the first surface, wherein the control zone is capable of indicating a positive control for the device. The control zone is preferably positioned downstream, that is further down the liquid flow path, than the first surface. See, for example, FIG. 1. One function of the control zone is to ensure that the liquid sample has proceeded completely through its flow path to the end portion of the device. This function serves to eliminate false negative tests due to disruptions in the sample flow path such that the sample does not reach the detecting complex immobilized on the first surface.

In one embodiment, the control zone contains a control binding partner coupled to a detectable entity, wherein the control binding partner binds a substance that is normally present in the sample being tested and is other than the target analyte. By way of example, a device designed for testing blood samples can have a control zone comprising a control binding partner coupled to a detectable entity that binds to a red blood cell antigen. Alternatively, the control binding partner can bind a compound that has been artificially supplied to the sample. This artificially added compound can be added to the sample prior to application of the sample to the device or it can be dried into the sample pad or reagent pad. For purposes of illustration, a control binding partner can be streptavidin that would bind biotin that had been artificially added to the sample or dried into the sample pad. In another embodiment, the control zone contains a control binding partner which specifically binds or captures unbound or overflowing (e.g., from detection zone) first or second binding partner, e.g., antibody against the first or second binding partner.

In particular embodiments, the control binding partner coupled to a detectable entity is immobilized to the surface of the control zone. Preferably, the detectable entity coupled to the control binding partner in the control zone is the same as the detectable entity in the detecting complex. In some embodiments, gold nanoparticles for use as the detectable entity in both the detecting complex and control zone are preferred.

The present invention also provides an analyte detection device for detecting multiple target analytes in the same sample. In one embodiment, the device comprises a first detecting complex and a second detecting complex immobilized on at least one surface, wherein the first detecting complex comprises a first binding partner coupled to a first detectable entity and the second detecting complex comprises a second binding partner coupled to a second detectable entity. The first binding partner is capable of forming a complex with a first target analyte, while the second binding partner is capable of forming a complex with a second target analyte. Preferably the first and second detecting complexes are formed prior to immobilization to the at least one surface.

The first target analyte and the second target analyte can be present in the same sample. In some embodiments, the sample is a biological sample. Additional detecting complexes (e.g. a third detecting complex, fourth detecting complex, etc.) can be immobilized on at least one surface to extend the capability of the device to detect multiple analytes simultaneously. The additional detecting complexes can each contain binding partners coupled to detectable entities, wherein each of the binding partners bind a different target analyte.

In some embodiments, the first detectable entity and the second detectable entity are metallic nanoparticles or metallic nanoshells. The first detectable entity and the second detectable entity can be the same type of metallic nanoparticle or metallic nanoshell (e.g. both gold nanoparticles) or they can be different types of metallic nanoparticles or metallic nanoshells (e.g. one gold nanoparticle and one silver nanoparticle). In the latter embodiment, the detection of a particular analyte would be associated with a particular type of color change dependent on the type of metallic nanoparticle or metallic nanoshell employed as the detectable entity. Additional detecting complexes that can be incorporated into the device can comprise the same detectable entity or a different detectable entity than the detectable entities contained within the pre-existing detectable complexes.

Figure 2:
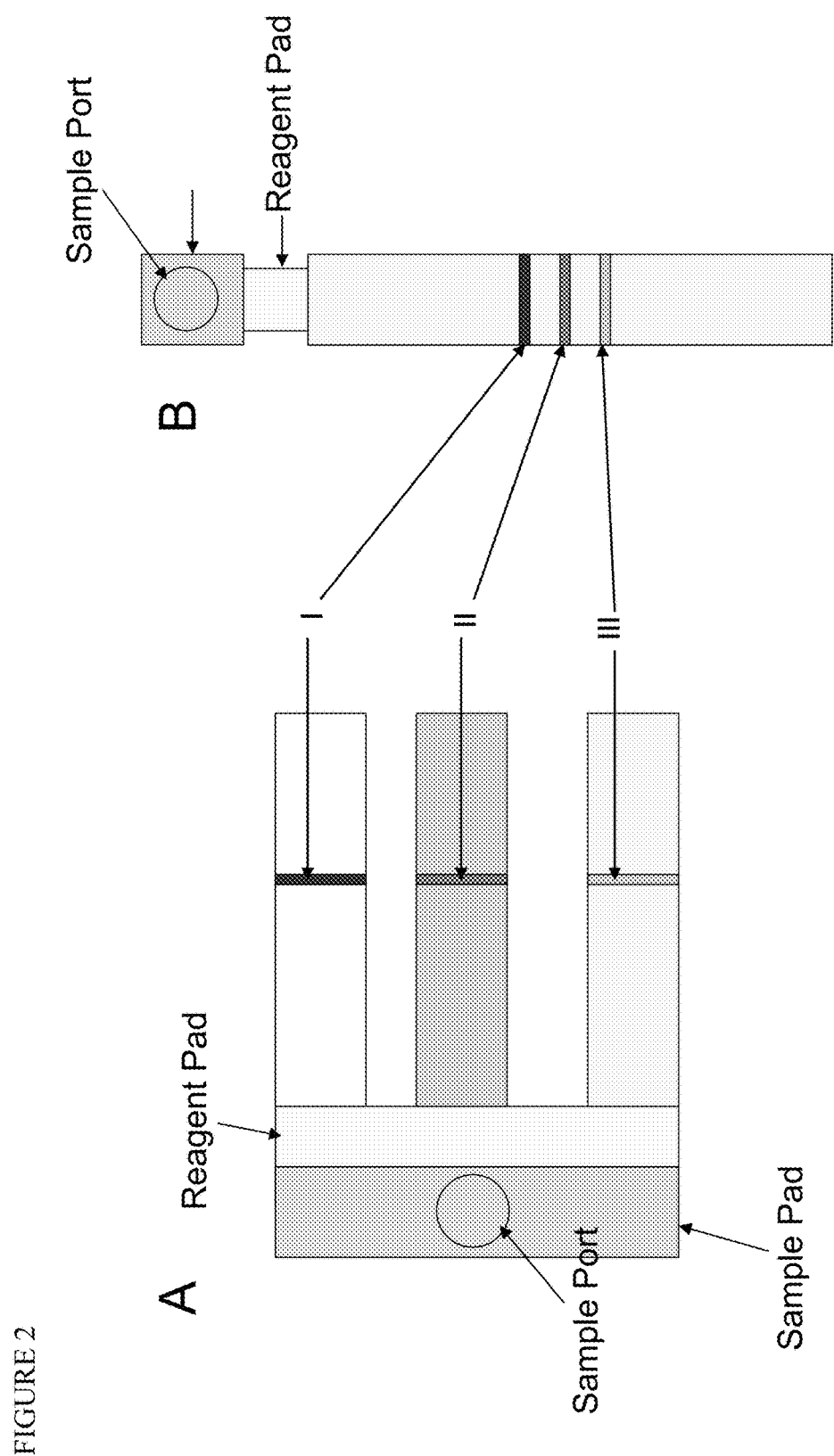
FIG. 2 illustrates two configurations of a multiple analyte detection device of the invention.

Various configurations of the multiple immobilized detecting complexes within the device are contemplated by the present invention. In one embodiment, the first detectable complex and the second detectable complex are immobilized on the same surface. See, for example, FIG. 2B. In this configuration, sample is applied to the device at one end of the surface and flows through each of the different detectable complexes sequentially. In another embodiment, the device further comprises a second surface adjacent to the first surface, wherein the first detectable complex is immobilized on the first surface and the second detectable complex is immobilized on the second surface. Additional surfaces can be incorporated into the device to accommodate the addition of other detectable complexes. Therefore, if the device were designed to detect three distinct target analytes, then the device can comprise three surfaces with a separate detecting complex immobilized to each of the three surfaces. This type of configuration is illustrated in FIG. 2A. In this type of device, sample can be added to a sample pad, which is upstream of and in fluid communication with the multiple surfaces. The sample will split into multiple flow paths and travel to each of the separate detecting complexes immobilized on separate surfaces.

Sample pads, reagent pads, and absorbent pads as described herein can be incorporated into the multiple analyte detection device in any combination. The only requirement is that each of the components be in fluid communication with the surface or surfaces comprising the detecting complexes. Similarly, one or more control zones can also be included in the multiple analyte detection device. By way of example, a device that comprises two or more surfaces can contain two or more control zones, one connected to each surface, to ensure that the sample flow paths on each surface are sufficient to contact each of the detecting complexes.

Any of the devices disclosed herein can be positioned in an enclosed housing. Preferably the housing is constructed from a type of plastic material. The housing should not interfere with the flow paths of the sample between the components of the device or impair sample application or the reading of the results. In one embodiment, the housing comprises a sample port positioned over the sample pad. In another embodiment, the housing comprises a test window positioned over the first surface. When multiple surfaces are present in the device as in particular configurations of the multiple analyte detection device, the housing can comprise a test window that extends over the multiple surfaces. The housing can include one or more vents to facilitate fluid movement through the device. In some embodiments, the vents can be located in the housing forming the side walls of the device. In other embodiments, the vents can be positioned in the housing forming the top cover of the device.

The present invention also contemplates a method of detecting a target analyte in a test sample. In one embodiment, the method comprises contacting the test sample with the first surface of a device disclosed herein and detecting a signal corresponding to the binding of the target analyte to the detecting complex, wherein the presence of the signal is indicative of the presence of the target analyte. In another embodiment, the method comprises contacting the sample pad of a device disclosed herein with the test sample and detecting a signal corresponding to the binding of the target analyte to the detecting complex, wherein the presence of the signal is indicative of the presence of the target analyte. In still another embodiment, the method comprises contacting the test sample with the sample pad in a device described herein, wherein the test sample flows through the reagent pad prior to reaching the first surface, and detecting a signal corresponding to the binding of the target analyte to the detecting complex, wherein the presence of the signal is indicative of the presence of the target analyte.

A test sample can be any type of liquid sample, including biological samples or extracts prepared from environmental or food samples. In a preferred embodiment, the test sample is a biological sample. Biological samples include, but are not limited to, blood, plasma, serum, urine, sweat, bile, cerebrospinal fluid, fecal material, vaginal fluids, sperm, and saliva.

Any type of analyte can be detected using the methods of the present invention. An "analyte" refers to any substance capable of being bound by a binding partner of the detecting complexes disclosed herein. An analyte encompasses derivatives or metabolites of the compound of interest. In some embodiments, the analytes are associated with infectious diseases in both humans and animals. In other embodiments, the analytes are markers of a particular physiological or pathological condition. A target analyte can be a protein, peptide, nucleic acid, hapten, or chemical.

The signal corresponding to the binding of the target analyte to the detecting complex can be detected visually or by means of an instrument. In some embodiments, the signal is a spectral shift. In other embodiments, the signal is detected by measuring a change in absorbance of the signal. Commercial instruments capable of detecting spectral and electrochemical changes can be used measure the change in absorbance of the signal from the detecting complexes of the devices. Such instruments include "strip readers" and are know to those skilled in the art.

Figure 3:
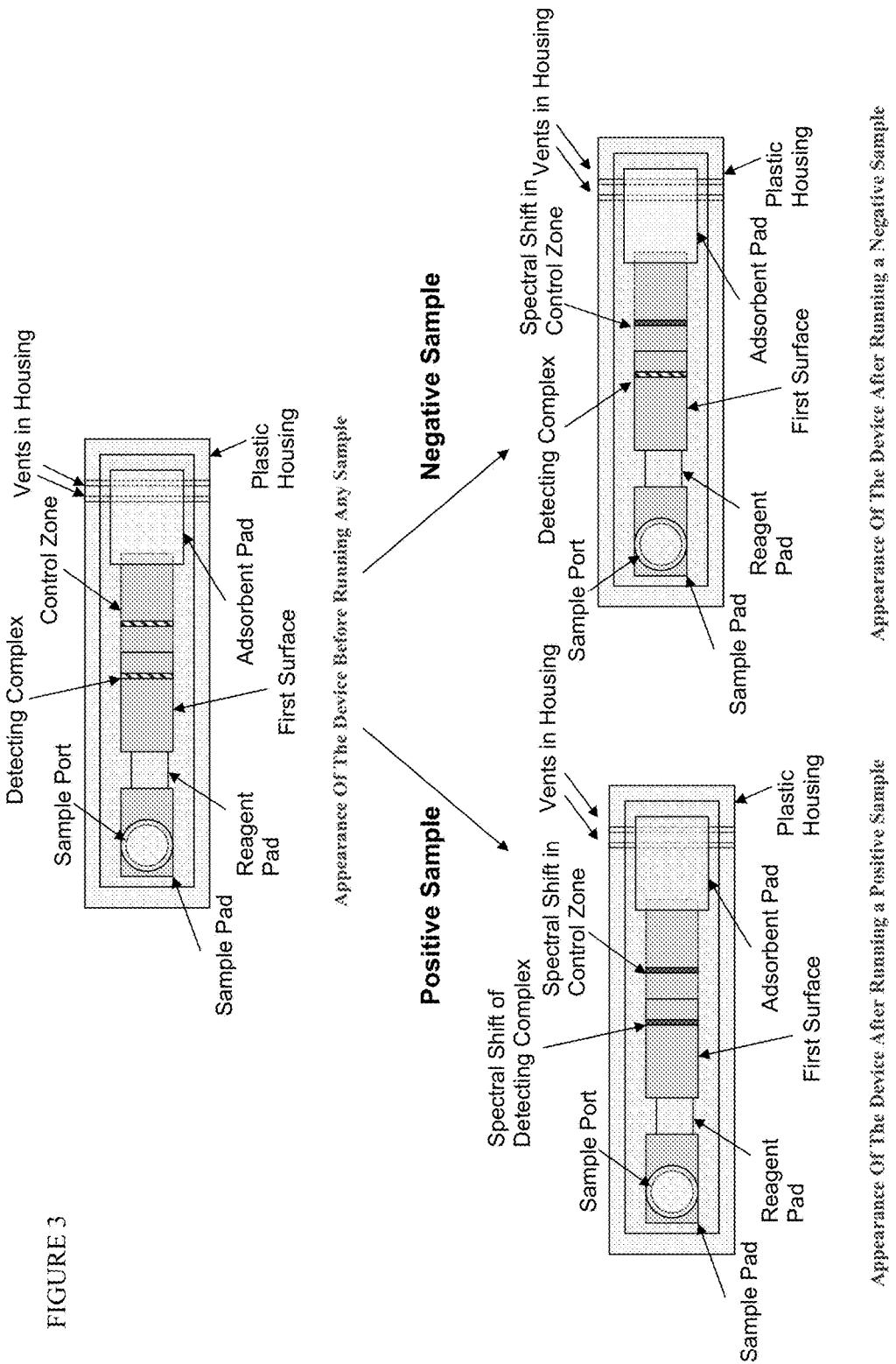
FIG. 3 depicts one configuration of the device of the present invention. The left hand side of the figure demonstrates the appearance of the device after a sample containing the target analyte (i.e. positive sample) is applied to the device. The right hand side of the figure demonstrates the appearance of the device after a sample that does not contain the target analyte (i.e. negative sample) is applied to the device. Hatched bars indicate the normal color of the detecting complexes on the first surface and in the control zone. Solid filled bars indicate a color change or spectral shift of the detecting complexes.

The presence of a signal, such as a spectral shift, is indicative of the presence of the analyte in the sample. FIG. 3 illustrates the method of using one embodiment of the device of the invention to detect a target analyte in a liquid sample. The appearance of a device is shown for both a sample that is negative for the target analyte and for a sample that is positive for the analyte. Sample is applied to the device through the sample port. Contact of the sample with the sample pad causes materials, such as buffers, detergents, blocking agents, neutralizing agents, and accelerants, dried into the sample pad to dissolve. The sample and dissolved components are then wicked into the reagent pad. In the absence of target analyte, no binding reaction with the second binding partner present in the reagent pad occurs, and the fluid moves to the first surface. In the presence of target analyte in the sample, a complex forms between the target analyte and the second binding partner. The complex is then wicked into the first surface. The complex between the analyte and second binding partner contact the immobilized detecting complex causing a spectral shift (e.g. color change). The fluid continues to move into the control zone, where either an artificially added component or natural component reacts with the immobilized control complex to induce a spectral shift in the control zone, indicating the successful performance of the device. The spectral shifts in both the control zone and the first surface will be clarified as the excess sample fluid moves into the absorbent pad. In the absence of a target analyte (negative sample), no complex is present to bind to the detecting complex immobilized on the first surface, so no spectral shift will be observed in this region. However, once the fluid contacts the immobilized detecting complex in the control zone, a spectral shift should be produced to indicate that the fluid flow through the device was adequate.

Any of the devices disclosed herein can be used in the methods of detecting a target analyte in a test sample. In some embodiments, the device used in the method comprises a first surface having an accelerant to accentuate the spectral shift of the detecting complex upon binding of the target analyte.

In some instances it can be desirable to amplify signals from the detecting complex or control zone. Accordingly, in another embodiment of the invention, the method further comprises contacting the sample pad with an enhancing agent. Alternatively, the enhancing agent can be applied directly to the first surface or control zone. An "enhancing agent" is a compound that amplifies the intensity of the signal from the detecting complex. Examples of suitable enhancing agents, particularly if the detectable entity is a gold nanoparticle, include silver nitrate, osmium tetroxide, diaminobenzidine, and tetrazolium dyes. In one embodiment, the enhancing agent is silver nitrate or osmium tetroxide. The application of enhancing agents can increase the sensitivity of the devices of the invention, thereby extending their application for particular analytes, especially those that are known to be present in very low concentrations.

In yet another embodiment, signal from the detecting complex is amplified via an enzymatic reaction, e.g., through the second binding partner. For example, the second binding partner can be coupled to or labeled with an enzyme, e.g., alkaline phosphatase, horse radish peroxidase, etc. and provide a signal upon exposure to the enzyme's corresponding substrate and such signal is in addition to the signal produced by the first binding partner upon binding to the target analyte. Alternatively, the first binding partner immobilized on the first surface can be coupled to or conjugated with an enzyme as well as a detectable entity as described in the present invention. For instance, the enzyme can be directly linked to the detectable entity, the first binding partner, or be encaged in a shell, e.g., metallic nanoshell. In some instances, the enzyme is encaged in a metallic nanoshell which is chemically linked or physically attached to the first binding partner.

The present invention also encompasses kits comprising the inventive devices disclosed herein. In one embodiment, the kit comprises an analyte detection device and instructions for using the device to detect an analyte in a test sample, wherein the device comprises a detecting complex immobilized on a first surface, said detecting complex comprising a first binding partner coupled to a detectable entity, said first binding partner being capable of forming a complex with the target analyte, and wherein the detecting complex is formed prior to being immobilized on the first surface. The kit can further include means for collecting biological samples or extraction buffers for obtaining samples from solid materials, such as soil, food, and biological tissues. In some embodiments, the kit can include enhancing agents to intensify the detectable signals of the device.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

The invention claimed is:

1. An analyte detection device comprising
   a sample pad; and
   a detecting complex immobilized on a first surface, wherein the detecting complex comprises a first binding partner coupled to a metallic nanoparticle or metallic nanoshell, wherein the first binding partner is immobilized directly to the first surface by covalent bonding, wherein the first binding partner forms a complex with an unlabeled target analyte, and wherein a spectral shift is indicative of the presence of the analyte; and
   wherein the sample pad is in operable fluid communication with the first surface.

2. The device of claim 1, wherein the first surface is a porous surface.

3. The device of claim 1, wherein the first surface is of nitrocellulosic material, polyvinylidene fluoride (PVDF), polyethylene material, nylon, cellulose acetate, polyester material, polyethersulfone (PES), or polysulfone.

4. The device of claim 1, wherein the first binding partner is an antibody, receptor, ligand, polynucleotide, polypeptide, glycopeptide, lipoprotein, or nucleoprotein.

5. The device of claim 1, wherein the metallic nanoparticle or metallic nanoshell is selected from the group consisting of gold particles, silver particles, copper particles, platinum particles, cadmium particles, composite particles, gold hollow spheres, gold-coated silica nanoshells, and silica-coated gold shells.

6. The device of claim 1, wherein the sample pad or the first surface, or both, comprises an accelerant, a blocking agent, a neutralizing agent, or a combination thereof.

7. The device of claim 6, wherein the accelerant is selected from the group consisting of polyethylene glycol, polyvinylpyrrolidone, polyvinyl alcohol, and mixtures thereof.

8. The device of claim 1, wherein the sample pad comprises one or more dried buffers or detergents or a combination thereof.

9. The device of claim 1, further comprising an adsorbent pad that is in operable fluid communication with the first surface.

10. The device of claim 1, further comprising a reagent pad that is in operable fluid communication with the first surface.

11. The device of claim 1, further comprising a reagent pad and an adsorbent pad, both of which are in operable fluid communication with the first surface.

12. The device of claim 10, wherein the reagent pad comprises a second binding partner capable of forming a complex with the target analyte and wherein the reagent pad is positioned between the sample pad and the first surface.

13. The device of claim 12, further comprising a control zone in operable fluid communication with the sample pad, reagent pad and the first surface, wherein the control zone is capable of indicating a positive control for the device.

14. The device of claim 1, wherein the device is positioned in an enclosed housing.

15. A method of detecting an unlabeled target analyte in a test sample comprising:
  contacting the test sample with the sample pad of the device of claim 1, and
  wherein the spectral shift is indicative of the presence of the unlabeled target analyte.

16. The method of claim 15, further comprising contacting the sample pad with an enhancing agent.

17. The method of claim 16, wherein the enhancing agent is silver nitrate or osmium tetroxide.

18. The method of claim 15, wherein the spectral shift is measured by change in absorbance.

19. The method of claim 15, wherein the test sample is a biological sample.

20. The method of claim 15, wherein the target analyte is a protein, peptide, nucleic acid, hapten, or chemical.

* * * * *